US006678049B1

(12) United States Patent
Painchaud (10) Patent No.: US 6,678,049 B1
(45) Date of Patent: Jan. 13, 2004

(54) OPTICAL DETECTION SYSTEM AND METHOD

(75) Inventor: Yves Painchaud, Sillery (CA)

(73) Assignee: ART, Advanced Research Technologies Inc., Montreal (CA)

( * ) Notice: Subject to any disclaimer, the term of this patent is extended or adjusted under 35 U.S.C. 154(b) by 0 days.

(21) Appl. No.: 09/984,171

(22) Filed: Jan. 25, 2002

Related U.S. Application Data
(60) Provisional application No. 60/305,098, filed on Jul. 16, 2001.

(51) Int. Cl.[7] .............................................. G01N 21/00
(52) U.S. Cl. ........................ 356/432; 356/434; 128/665
(58) Field of Search ................................. 356/336–343, 356/434, 39–41, 432; 600/407, 473, 476; 128/633, 644, 665, 897, 898; 250/358.1, 458.1

(56) References Cited

U.S. PATENT DOCUMENTS

| | | | | |
|---|---|---|---|---|
| 5,144,374 A | * | 9/1992 | Grego ........................ 356/326 |
| 5,386,819 A | * | 2/1995 | Kaneko et al. | |
| 5,477,051 A | * | 12/1995 | Tsuchiya ..................... 356/432 |
| 5,553,614 A | * | 9/1996 | Chance ........................ 128/633 |
| 5,692,504 A | * | 12/1997 | Essenpreis et al. ............ 356/39 |
| 5,836,883 A | * | 11/1998 | Tsuchiya et al. ............... 356/39 |
| 5,899,865 A | * | 5/1999 | Chance ........................ 600/473 |
| 6,321,111 B1 | * | 11/2001 | Perelman et al. ......... 250/358.1 |

OTHER PUBLICATIONS

D. Grosenick, et al., Time–resolved imaging of solid phantoms or optical mammography; Applied Optics, vol. 36, No. 1, pp. 221–232, Jan. 1, 1997.

Dirk Grosenick, et al., Development of a time–domain optical mammograph and first in vivo applications; Applied Optics; vol. 38, No. 13, pp. 2927–2941, May 1, 1999.

K.M. Yoo, et al., Imaging of a translucent object hidden in a highly scattering medium from the early portion of the diffuse component of a transmitted ultrafast pulse, Optic Letters, vol. 17, No. 13, pp. 958–960, Jul. 1, 1992.

Marcia L. Vernon, et al, Fabrication and characterization of a solid polyurethane phantom for optical imaging through scattering media, Applied Optics, vo. 38, No. 19, pp. 4247–4251, Jul. 1, 1999.

B.B. Das, et al., Ultrafast time–gated imaging in thick tissues: a step toward optical mammography, Optics Letters, vol. 18, No. 13, pp. 1092–1094, Jul. 1, 1993.

Yves Painchaud, et al., Time–domain optical imaging: discrimination between scattering and absorption, Applied Optics, vol. 38, No. 16, pp. 3686–3693, Jun. 1, 1999.

Jeremy C. Hebden, Evaluating the spatial resolution performance of a time–resolved optical imaging system, Med. Phys, 19(4), pp 1081–1086, Jul./Aug. 1992.

Jeremy C. Hebden, et al. the spatial resolution performance of a time–resolved optical imaging system using temporal extrapolation, Med. Phys. 22(2), pp 201–208, Feb. 1995.

S.B. Colak, et al., Tomographic image reconstruction from optical projections in light–diffusing media, Applied Optics, vol. 36, No. 1, pp. 180–213, Jan. 1, 1997.

S.K. Cayen, et al., Emerging optical biomedical imaging techniques, Optics & Photonics News, Mar. 1996.

* cited by examiner

*Primary Examiner*—Frank G. Font
*Assistant Examiner*—Sang H. Nguyen
(74) *Attorney, Agent, or Firm*—Olilvy Renault; James Anglehart

(57) ABSTRACT

An optical imaging system for detecting light from an excitation light source through a scattering medium. The system includes a photo detector for receiving light from the scattering medium, an amplification circuit coupled from the photo-detector, an electro-optical source coupled from the amplification circuit for providing a secondary light signal, and a streak camera receiving the secondary light signal and providing an image of the scattering medium.

38 Claims, 6 Drawing Sheets

OPTICAL DETECTION SYSTEM AND METHOD

This application claims the benefit of Provisional application Ser. No. 60/305,098, filed Jul. 16, 2001.

TECHNICAL FIELD

The present invention relates in general to an apparatus and associated method for detecting light transmitted through a scattering medium. More particularly, the present invention relates to a detection system and method using time-resolved tissue transillumination. The invention may be employed for tumor detection using a time-resolved breast transillumination technique.

BACKGROUND OF THE INVENTION

Optical imaging of turbid media such as the human breast has been the subject of much research activity and has seen an increase in interest since the early 1990s. This type of imaging is based on the fact that the propagation of light in a turbid medium depends on the absorption and scattering properties of the medium. Absorption results from energy level transitions of the constituent atoms and molecules in the medium. The absorption property of the medium is quantified by its absorption coefficient $\mu_a$, defined as the probability of a photon being absorbed per infinitesimal pathlength. Scattering results from variations in the index of refraction of the different structures present in the medium. In a highly diffusive medium, scattering is quantified by the reduced scattering coefficient $\mu_s'$ defined as the probability of a photon being isotropically scattered per infinitesimal pathlength. Characteristics such as intensity, coherence and polarization of the incident light change as it is absorbed and scattered by the medium resulting in diffuse transmittance of the light. In particular, scattering causes a collimated laser beam to spread over a sizeable volume element. This complicates the imaging of a turbid medium. Special imaging modalities must be implemented to offset the detrimental light diffusion. For example, time-resolved methods use ultra-short laser pulses to illuminate the medium. The emergent light is collected by a fast detector capable of reproducing its time variation, which can provide further information about the turbid medium. A simple data processing approach in this case is time-gating, by which only the earliest part of the output light pulses is used to produce an image. Refer to article S. K. Gayen and R. R. Alfano, "Emerging optical biomedical imaging techniques," *Opt. & Photon. News*, 7, pp. 7–22 (1996). This amounts to using only the light with the straightest trajectory through the scattering medium, thus improving spatial resolution. See the articles: J. C. Hebden, "Evaluating the spatial resolution performance of a time-resolved optical imaging system," *Med. Phys*, 19, pp. 1801–1087 (1992) and J. C. Hebden, D. J. Hall, and D. T. Delpy, "The spatial resolution performance of a time-resolved optical imaging system using temporal extrapolation" *Med. Phys.*, 22, pp. 201–208 (1995).

The strong interest in optical imaging of scattering media stems from the need for biomedical diagnostic techniques that are safe and non-invasive. The optical properties of biological tissues are at the heart of optically based biomedical diagnostic techniques. As for the general case of a turbid medium, the manner in which light propagates through tissue depends on its absorption and scattering properties. Thus, if abnormal tissue can be said to differ from normal in its absorption or scattering of light for some physiological or morphological reason, it then becomes possible to optically differentiate between normal and abnormal conditions. A specific application is optical mammography where tumors could be differentiated from normal breast tissue on the basis of optical properties.

Mainly two types of biomedical optical imaging exist: tomography and transillumination. Tomography is typically based on a multi-point geometry involving a large number of detectors and allows the reconstruction of 3D images. Refer to the article S. B. Colak, D. G Papaioannou, G. W. Hooft, M. B. Van der Mark, H. Schomberg, J. C. J. Paasschens, J. B. M. Melissen, and N. A. A. J. Van Asten, "Tomographic image reconstruction from optical projections in light-diffusing media," *Appl. Opt.*, 36, 180–213 (1997). Obtaining 3D information is an important advantage of tomography, however, measurements and reconstructions are potentially time-consuming.

Transillumination (or 2D projection imaging) refers to a scanning procedure in which each image pixel is determined from the detection of the light that enters the medium through a certain entrance area, that propagates through it and that exits over a certain detection area usually facing the entrance area. The light entering the medium is generated by an excitation light source, typically a laser source emitting a laser beam at a wavelength in the range of 700–850 nm. The absorption of light by the tissues is minimal within this wavelength range.

Figure 1:
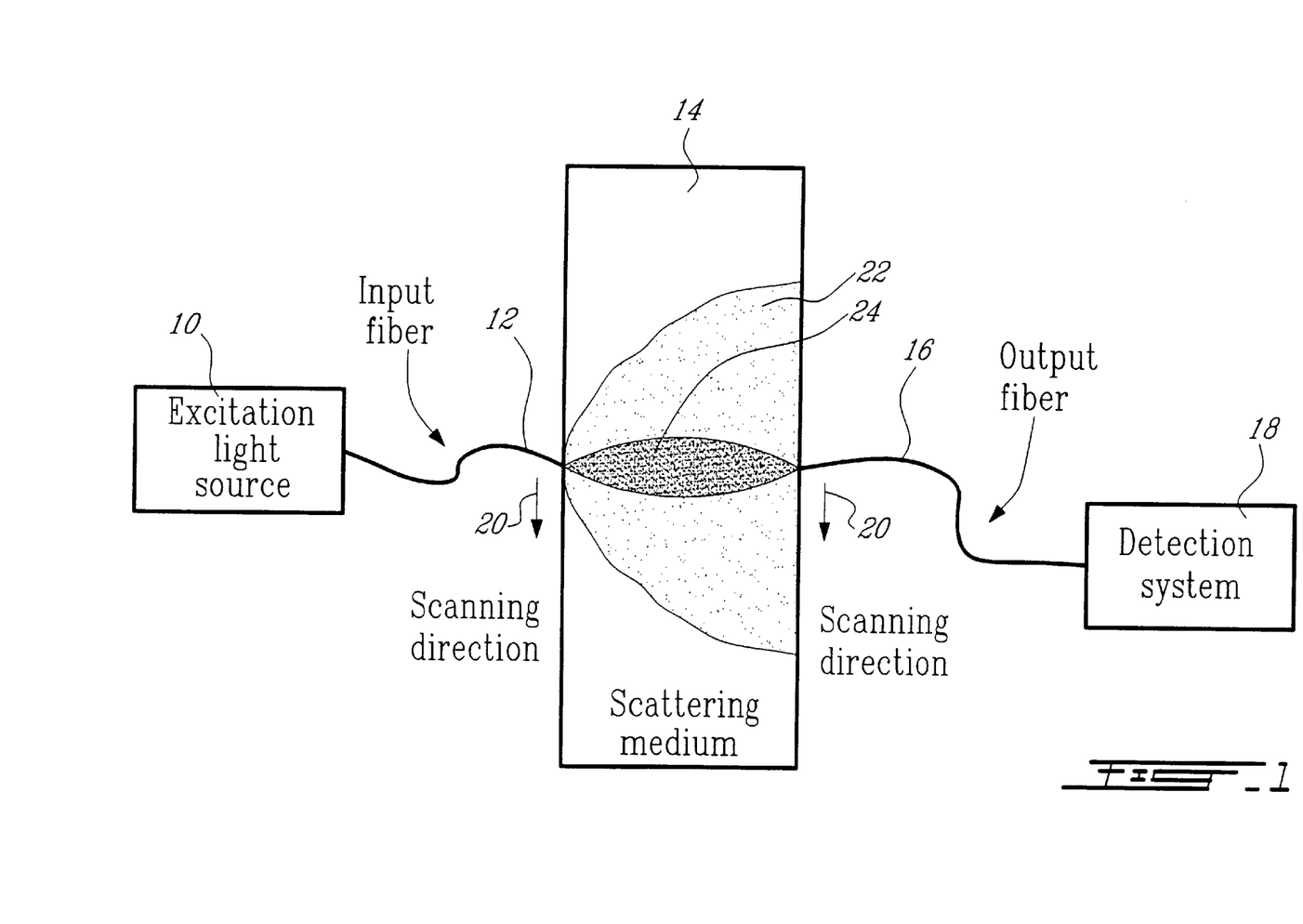
FIG. 1 is a block diagram of a scanning system for imaging through turbid media.

A typical apparatus for obtaining transillumination images is illustrated in FIG. 1. This system typically includes an excitation light source 10, an input fiber 12, the scattering medium 14, an output fiber 16, and the detection system 18. FIG. 1 also shows at 20, the scanning direction.

The gray zone 22 in FIG. 1 indicates the volume through which the photon travel before emerging to the output surface, while the dark zone 24 indicates the same but for the limited fraction of photon that are detected. As shown in FIG. 1, optical fibers can be used to facilitate the scanning of the input beam and the area over which the output light is collected.

The adverse effect of light scattering can be alleviated by detecting the light in a time-resolved manner. For example, at each point of a transillumination scan, an ultra-short laser pulse (typically <0.5 ns) can be injected at an input surface of the scattering medium. The light emerging from the opposite surface can be detected as a function of time, on a nanosecond range. This can be repeated a large number of cycles within a certain time integration in order to accumulate a sufficient photon statistics. The resulting time-resolved measurement typically appears as a vector of light intensity for different time values.

From each vector, a scalar must be calculated and transformed into a pixel value. A different method can be used for the calculation of such a scalar number. The sum of all the vector values can be performed and the resulting Continuous Wave (CW) image would be the same as obtained with a CW optical imaging transillumination technique. The sum can also be limited to the first time values which correspond to considering only the first arrival photons which experienced less diffusion and providing a less blurred image compared to a CW image. See the article: B. B. Das, K. M. Yoo, and R. R. Alfano, "Ultrafast time-gating imaging in thick tissues: a step toward optical mammography" *Opt. Lett.*, 18, pp. 1092–1094 (1993). More sophisticated techniques can also be used as described in the article: Y. Painchaud, A. Mailloux, M. Morin, S. Verreault, and P. Beaudry, "Time-domain opticalimaging: discrimination between scattering and absorption," *Appl. Opt.*, 38, pp. 3686–3693 (1999).

For obtaining a good spatial resolution, the detection of the emerging light is typically done over a detection area which is small compared to the area from which the light emerges at the output surface. However, the detection of light over a large area is beneficial in order to increase the number of detected photons and thus the signal-to-noise ratio. A detection area on the order of 10 mm² appears to be a good compromise. The detection system has to measure the emerging light intensity over a certain area and with a certain time resolution. Assuming that the entire time-distribution of the emerging light is of interest and that the injected laser power is 50 mW at 800 nm, the requirements of an ideal detection system are the following:

Large area (~10 mm²);

High numerical aperture (~0.4);

Fast time-response (<0.5 ns);

High quantum efficiency at 800 nm (as high as possible);

High dynamic range ($10^{-8}$ to $10^{31\ 3}$ W/cm²).

Two main detection systems have been used in reported studies involving time-resolved detection of scattered light: streak cameras; see the following article: K. M. Yoo, B. B. Das, and R. R. Alfoano, "Imaging of a translucent object hidden in a highly scattering medium from the early portion of the diffuse component of a transmitted ultrafast laser pulse," Opt. Lett., 17, pp. 958–960 (1992) and photon counting systems; see the article: D. Grosenick, H. Wabnitz, and H. Rinneberg, "Time-resolved imaging of solid phantoms for optical mammography," Appl. Opt., 36, pp. 221–231 (1997).

The typical characteristics of a streak camera are the following:

Detection area: <1 mm²;

Numerical aperture: 0.2;

Time response: <0.1 ns;

Quantum efficiency: 10%;

Dynamic range: $10^{-7}$–$10^{-3}$ W/cm² and the typical characteristics of a photon counting system are:

Detection area: >10 mm²;

Numerical aperture: 0.4;

Time response: <0.5 ns;

Quantum efficiency: 20%;

Dynamic range: 0–$10^{-11}$ W (0–$10^{-10}$ W/cm² for a detection area of 10 mm²), (0–$10^{-8}$ W/cm² for a detection area of 0.1 mm²).

A streak camera is typically not sufficiently sensitive to cover the entire range of light intensity. Furthermore, its detection area is small. A larger area would allow a better photon statistics.

Oppositely, a photon counting system has a larger detection area, but typically is of little use: the system is simply too sensitive and would saturate for typical conditions of operation. As a result, most of the time, the signal has to be attenuated before detection, which results in a loss of the photon statistics. Using a photon counting system, acquisition time per pixel of less than 100 ms appears difficult. See the article D. Grosenick, H. Wabnitz, H. Rinneberg, K. T. Moesta, and P. M. Schlag, "Development of a time-domain optical mammograph and first in vivo applications," Appl. Opt., 38, pp. 2927–2943 (1999).

SUMMARY OF THE INVENTION

In accordance with the present invention there is provided an optical imaging system for detecting light from an excitation light source and passing through a scattering medium at a plurality of detection positions. The optical imaging system comprises a photo-detector for receiving light from the scattering medium and having sensitivity in a range of intensity of interest, and an amplification circuit that is coupled from the photo-detector. An electro-optical source is coupled from the amplification circuit and converts the electrical signal into a secondary light signal. A camera receives the secondary light signal and has high temporal resolution. The system provides the secondary light signal with an intensity suitable for good signal-to-noise quality detection by the camera for the range of intensity of interest.

In accordance with another aspect of the present invention there is provided a detection apparatus operated in accordance with a time-resolved transillumination technique. This apparatus may be used for breast tumor detection. The photo detector is preferably a fast photo detector with a large detection area generally greater than 1 mm² with a time response less than 500 ps. The electro-optical source may also have a time response less than 500 ps.

In accordance with another aspect of the present invention the camera is preferably a streak camera that allows recording of the time dependence of the light emerging from the electro-optical source with a time resolution less than 500 ps. The photo detector may comprise a photo-multiplier tube. The electro-optical source may comprise either a light-emitting diode or a laser diode.

In accordance with still another aspect of the present invention the system may include a primary output fiber for coupling from the scattering medium to the photo detector, and a secondary output fiber for coupling from the electro-optical source to the streak camera. The primary output fiber is larger in diameter than the secondary output fiber. The light detected at the primary output fiber is detected over a relatively large area, at least 1 mm² and is preferably on the order of 10 mm². The secondary output fiber is small compared to the primary output fiber whereby only a small fraction of the detection area of the streak camera is used.

In accordance with another embodiment of the present invention there is provided a multi-channel optical-detection system for detecting light initated through a scattering medium from an excitation light source. This multi-channel optical detection system comprises multi-channel photo detector means for receiving light from the scattering medium and a multi-channel electro-optical converting means for converting multiple electrical signals to separate multiple secondary light signals. A camera receives the multiple secondary light signals to provide an image of the scattering medium.

In accordance with still further aspects of the present invention the multi-channel photo detector means may comprise a single multi-channel photo detector. The photo detector may comprise a photo-multiplier tube including multiple anodes. A plurality of amplifier circuits interconnect the photo detector and the multi-channel electro-optical converting means. The electrico-optical converting means may comprise a plurality of light emitting diodes or a plurality of laser diodes.

In accordance with another embodiment of the present invention there is provided a method of detection of a transillumination image from a scattering medium. This method comprises the steps of, exciting the scattering medium from an excitation light source, followed by photo-electrically detecting the light from the scattering medium to provide an analog electrical signal. Next, is electro-optically converting the analog electrical signal to a secondary light signal. A camera is provided for receiving the secondary light signal and providing an image of the scattering medium.

In accordance with further aspects of the present method, there is included the step of amplifying the analog electrical signal between the steps of photo-electrically detecting and electro-optically converting. The detection is in a time-resolved manner. The step of photo-electrically detecting includes coupling the detected light by way of a primary optic fiber, and the step of electro-optically converting includes coupling the secondary light signal by way of the secondary optic fiber. The step of photo-electrically detecting may include coupling the detected light by way of a multi-channel photo-detector with multiple primary optic fibers coupling thereto. The step of electro-optically converting may include coupling the secondary light signal by way of a multi-channel source with multiple secondary optic fibers coupling therefrom. The step of providing a camera may include providing only a single camera accepting the multiple secondary optic fibers.

DESCRIPTION OF DRAWINGS

Numerous other objects, features and advantages of the invention should now become apparent upon a reading of the following detailed description when taken in conjunction with the accompanying drawings, in which:

FIG. 3 is a schematic block diagram of a detection scheme in accordance with the present invention for a multi-channel arrangement;

DETAILED DESCRIPTION OF PREFERRED EMBODIMENTS

The apparatus or system of the present invention is for detecting, in a time-resolved manner, the light transmitted through a scattering medium such as the human breast. The apparatus allows a collection of the light emerging from the medium over a relatively large surface and with a relatively large numerical aperture. This surface area is generally considered to be greater than 1 $mm^2$ and usually is up to several $mm^2$. The numerical aperture may be in a range up to 0.4.

One of the characteristics of the system of the present invention is that the detection apparatus does no saturate for the entire range of operation. As a result, no attenuation is required, thus allowing for an efficient photon statistics. Such a detection system permits a decrease in the duration of a time-resolved breast transillumination scan. Such a scan may be accomplished in only a few seconds.

The present invention combines the advantages of photon counting systems and streak-cameras. It uses a streak camera and a fast photo-detector typically used in a photon counting system. This fast photo-detector can be, as an example, a PMT detector (photo-multiplier tube). The output electrical current from the fast photo-detector is not compared to a threshold value and digitized as in a photon counting system. It is rather amplified analogically and used for driving a light source such as an ultrafast LED or an ultrafast diode-laser. The beam from this light source is sent to a streak camera which records the light intensity as a function of time with a high temporal resolution. Such a detection system is illustrated in FIG. 2.

In accordance with the detection scheme of the present invention, particularly as compared to the use of a streak camera alone, it is noted that in the present invention detection scheme the time resolution is reduced by the use of a fast photo-detector, an amplification circuit, and a light source, all having a certain time response. It is quite feasible to choose components such that the overall time response of the detection system is below 0.5 ns. Such a time response is quite suitable for time-resolved breast transillumination.

Figures 5A, 5B:
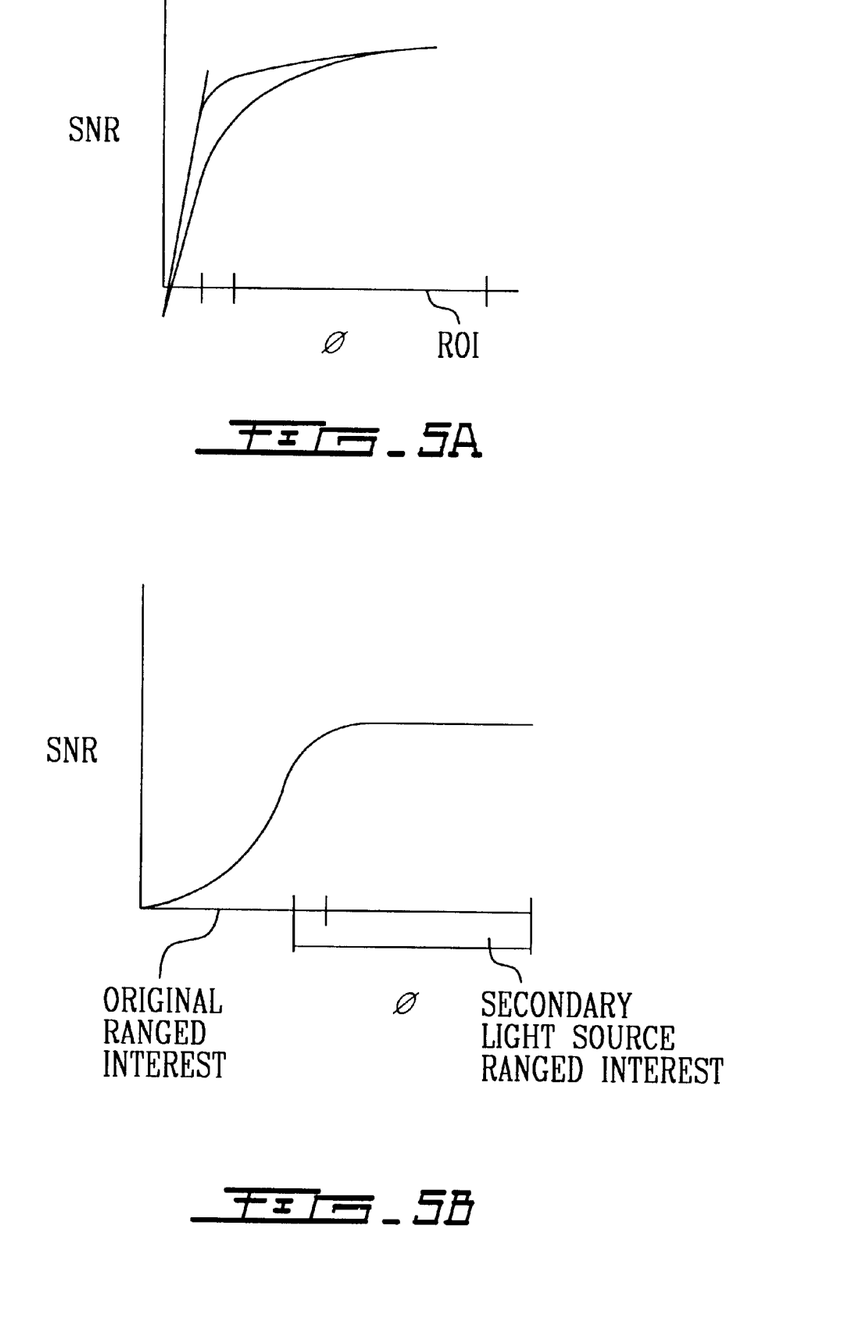
FIG. 5a is a graph of SNR of the fast photo-detector over the range of interest.
FIG. 5b is a graph of SNR of the camera over the range of interest.

Reference is now made to FIG. 5a and FIG. 5b showing respective signal-to-noise ratios for the fast photo-detector and the streak camera. In FIG. 5b it is noted that the original range of interest is depicted at the beginning portion of the curve and the secondary light source range of interest is at the flattened maximum amplitude portion of the graph.

Figure 2:
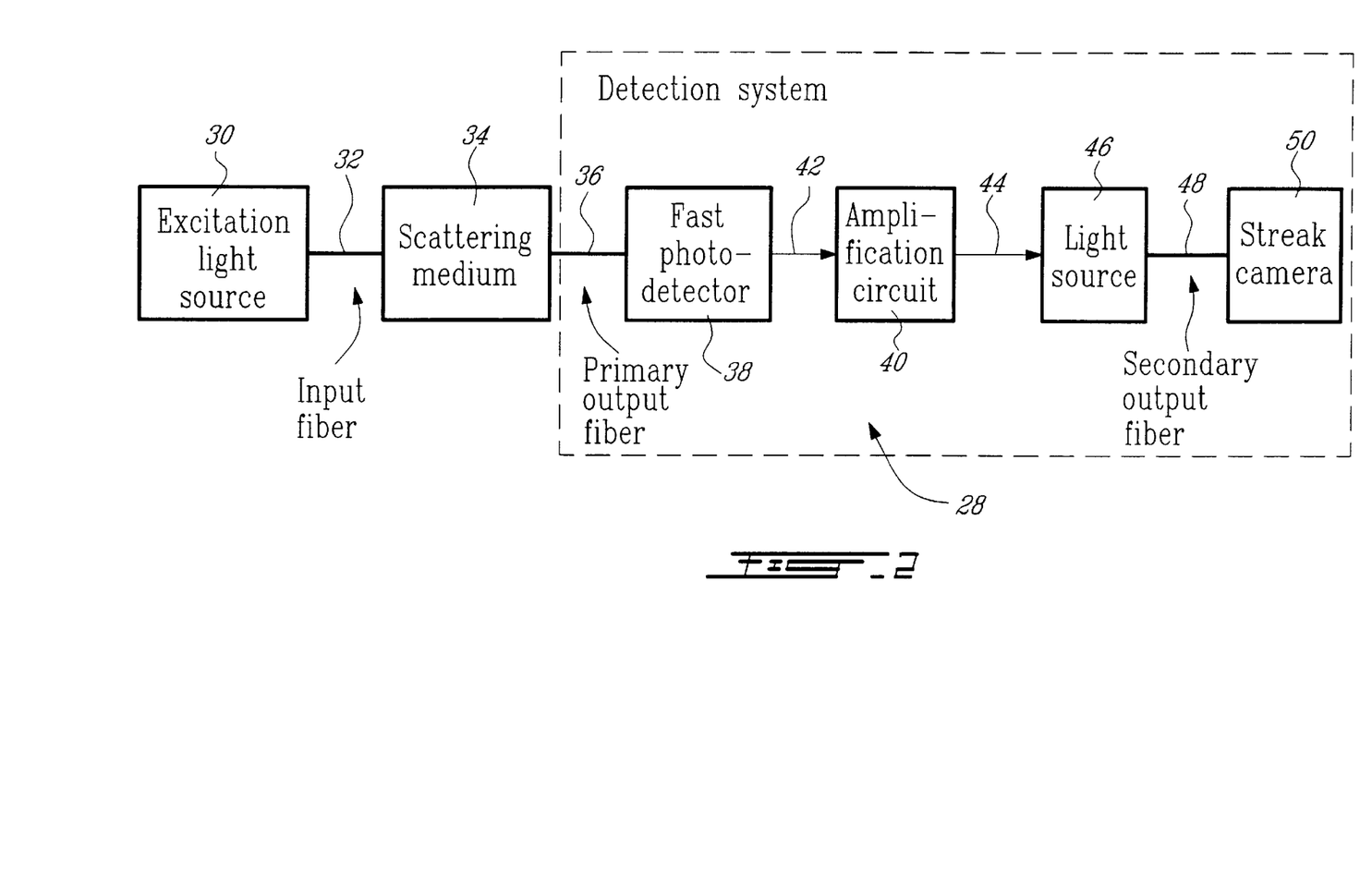
FIG. 2 is a schematic block diagram of a detection scheme in accordance with the present invention.

Reference is now made to the schematic block diagram of FIG. 2 that illustrates an excitation light source 30 coupling by way of an input fiber 32 to the scattering medium 34. In accordance with one use of the detection scheme for the present invention, the scattering medium may be a breast. FIG. 2 also illustrates the detection system 28, and more particularly, a primary output fiber 36 that couples to the photo-detector 38. The photo-detector 38 provides a photo-electric conversion with the output signal on line 42 coupling by way of amplification circuit 40 to the light source 46. The output line 44 couples to light source 46. The output of the light source 46 is a secondary output fiber 48 coupling to the streak camera 50.

Thus, the output electric current from the fast photo-detector 38 is amplified and analogically used for driving the light source 46 by way of the amplification circuit 40. The light source 46 may be an ultrafast LED or an ultrafast diode-laser. The beam from this light source is sent to the streak camera 50 which records the light intensity as a function of time with a high temporal resolution.

One important aspect of the present detection scheme is that the light is detected over a relatively large area, such as, for example, 10 $mm^2$. The detected light is converted into an electrical signal at the photo-detector 38 and reconverted into a light signal at the light source 46. This light signal is injected into the secondary output fiber 48 whose core can be relatively small. In one example even a 10 $\mu m$-core single-mode fiber may be used. In this way, only a small fraction of the detection area of the streak camera is used.

Since, in a streak camera, the light entering the input slit is spatially resolved along one axis, its detection area may be filled by a plurality of optical fibers such as in the multi-channel configuration of the present invention as illustrated in the schematic block diagram of FIG. 3. In this embodiment there is an excitation light source 130 with multiple input fibers 132 coupling to the scattering medium 134.

There are a like number of multiple primary output fibers 136 coupling to the multi-channel photo-detector 138. Separate outputs at 142 couple to a plurality of amplification circuits 140. The outputs of the amplification circuits 144 couple to multiple light sources 146. At the output of the light sources there are secondary output fibers 148 coupling to preferably a single streak camera 150.

In this multi-channel collection system of FIG. 3, a single streak camera 150 serves all of the channels. This is thus an optimized use of the streak camera whose cost is significantly higher than the rest of the elements of the detection system. Also, in the multi-channel system of FIG. 3, the detector 138 may be a multi-anode photo-multiplier tube. Alternatively, a plurality of fast photo-detectors can be used instead of a single, multi-channel fast photo-detector.

The following sets forth further specific parameters of the present invention, particularly as relates to the schematic block diagram of FIG. 2. The light emerging from the scattering medium may be collected by the use of a 3 mm diameter fiber bundle having a filling factor of about 75%. The photo-detector 38 may be a photo-multiplier tube, model R7400-02 from Hamamatsu. The anode current from the photo-multiplier tube detector is amplified and adapted for the purpose of driving a fast LED such as a model 1A363. The light emitted by the LED is directed to a streak camera such as the Hamamatsu model 5680-34. The secondary output fiber to the streak camera may be an optical fiber having a 50 $\mu$m-diameter core.

The performance of this system, referred to as the new detection system, was compared to a comparison detection system. In this comparison detection system, the light emerging from the scattering medium was collected by an optical fiber having a 400 $\mu$m-diameter core and carried to the same streak camera model C5680-34 from Hamamatsu. The entrance slit of the streak camera was completely opened so that the photocathode was illuminated on its entire width (160 $\mu$m). Thus, an effective detection area was approximately 160 $\mu$m×400 $\mu$m=0.064 mm$^2$.

The improvement in the detection sensitivity was evaluated in two ways, both in a CW regime (i.e. using the average detected light and not time-resolved). The sensitivities of the new detection system and the comparison detection system were compared in a CW regime in order to eliminate the influence of the different system time responses. In a first experiment, a plastic phantom containing an inclusion was scanned using the two detection systems. The resulting images were compared. A second series of experiments involved noise measurement used for anticipating the dynamic range of the two detection systems.

A polyurethane plastic phantom was built using a procedure described in the following article M. Vernon, J. Fréchette, Y, Painchaud, S. Caron, and P. Beaudry, "Fabrication and characterization of a solid polyurethane phantom for optical imaging through scattering media," *Appl. Opt.*, 38, pp. 4247–4251 (1999). The phantom was composed of a homogeneous scattering material ($\mu_s'$=0.8 mm$^{-1}$, $\mu_a$=0.005 mm$^{-1}$) containing a small inclusion of different optical properties ($\mu_s'$=1.0 mm$^{-1}$, $\mu_a$=0.014 mm$^{-1}$). The phantom was 240 mm×240 mm with a thickness of 64 mm. The inclusion was a 7 mm-thick 8 mm-diameter cylinder and its center was located at a depth of 5 mm inside the homogeneous plastic.

Figure 4A:
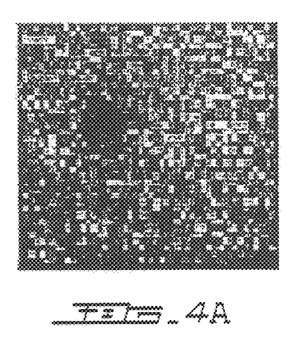
Fig. 4 illustrates some comparison images, useful in describing the concepts of the present invention.
Figure 4B:
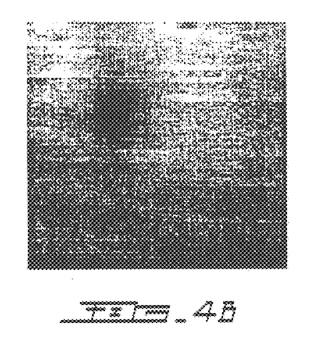
Figure 4C:
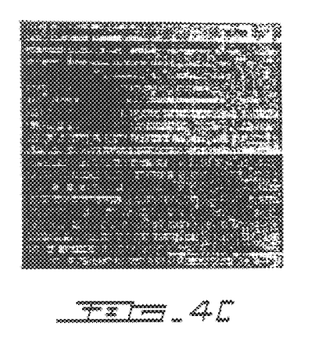

Transillumination CW images were obtained by procedures described hereinbefore. First, an image was obtained using the comparison detection system and a laser input power of 7 mW. In these conditions, the detected light was near the detection limit. A quite noisy image was obtained as shown in FIG. 4A. A second scan was done using the new detection system resulting in the CW image shown in FIG. 4B. As expected, the new detection system permits a significant improvement in the image quality. A third scan was done, again using the new detection system, when the laser unit power was decreased to 30 $\mu$W (a factor 230 with respect to 7 mW), resulting in the CW image shown in FIG. 4C. Considering that the image shown is FIG. 4C is less noisy than the one shown in FIG. 4A, one concludes that, compared to the comparison detection system, the new detection system allows an increase in sensitivity by a factor higher than 230.

The increase of the sensitivity is due to the detection of a larger number of photons. The use of the new detection system allows light emerging from the scattering medium to be collected over an effective area of 5.1 mm$^2$ and within a numerical aperture of 0.22. This is large compared to the comparison detection system in which the light is collected over an effective surface of 0.064 mm$^2$ within the same numerical aperture.

Noise measurements were performed as a way to characterize the detection over a broad range of input power. These measurements were done using the new detection system and the comparison detection system in a specific mode of operation (a time integration of 2 ns and an averaging over 2.67 millions of cycles.) The relative standard deviation was evaluated as a function of the input power for both systems. One can compare the sensitivity of the two systems from these measurements, and one can extrapolate what could be the dynamic range or the relative standard deviation for a system having a faster time response.

Figure 6:
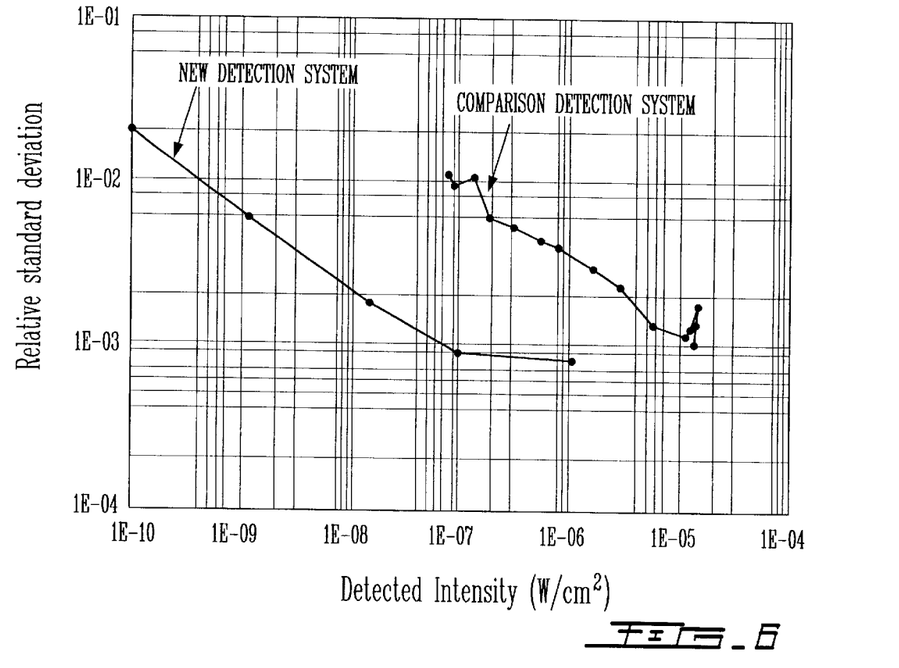
FIG. 6 is a graph relating relative standard deviation as a function of the input light intensity for the detection system of the present invention and for a comparison detection system.

Under continuous-wave excitation, weak levels of light were measured and integrated over a time interval of 2 ns within each cycle (in each cycle of 12.5 ns, the streak camera records detected light in a time-resolved manner.) The value of 2 ns was chosen as being larger than the time response of both the new and the comparison detection system. The streak camera, which can only record the temporal dependence of a repetitive signal, always performs an averaging over a minimum number of cycles. In the present situation, all the measurements were integrated over 2.67 millions of cycles which is equal to 1/30 s (the time integration of one video frame of the streak camera)×80 MHz (the frequency of the streak camera). Such a measurement, using the streak camera, was performed a large number of times allowing for the calculation of a relative standard deviation. For both the new and the comparison detection systems, the relative standard deviation was obtained in this manner as a function of the incident light intensity. The results are shown in FIG. 6.

As can be seen, these results demonstrate the significant improvement of the present invention compared to the comparison detection system. It can be seen in FIG. 6 that the sensitivity is improved by about 2 orders of magnitude lower than it is using the comparison detection system.

The time response of the comparison detection system was evaluated to be 150 ps by measuring the width of the detected signal obtained when an ultrashort laser pulse (<1 ps) was injected. The time response of the new detection system was evaluated to be 1.8 ns assuming a quadratic summation of the different component time responses given in Table 1. A time-resolved transmittance was measured through a homogeneous part of the phantom using both the comparison detection system and the new detection system.

Figure 7:
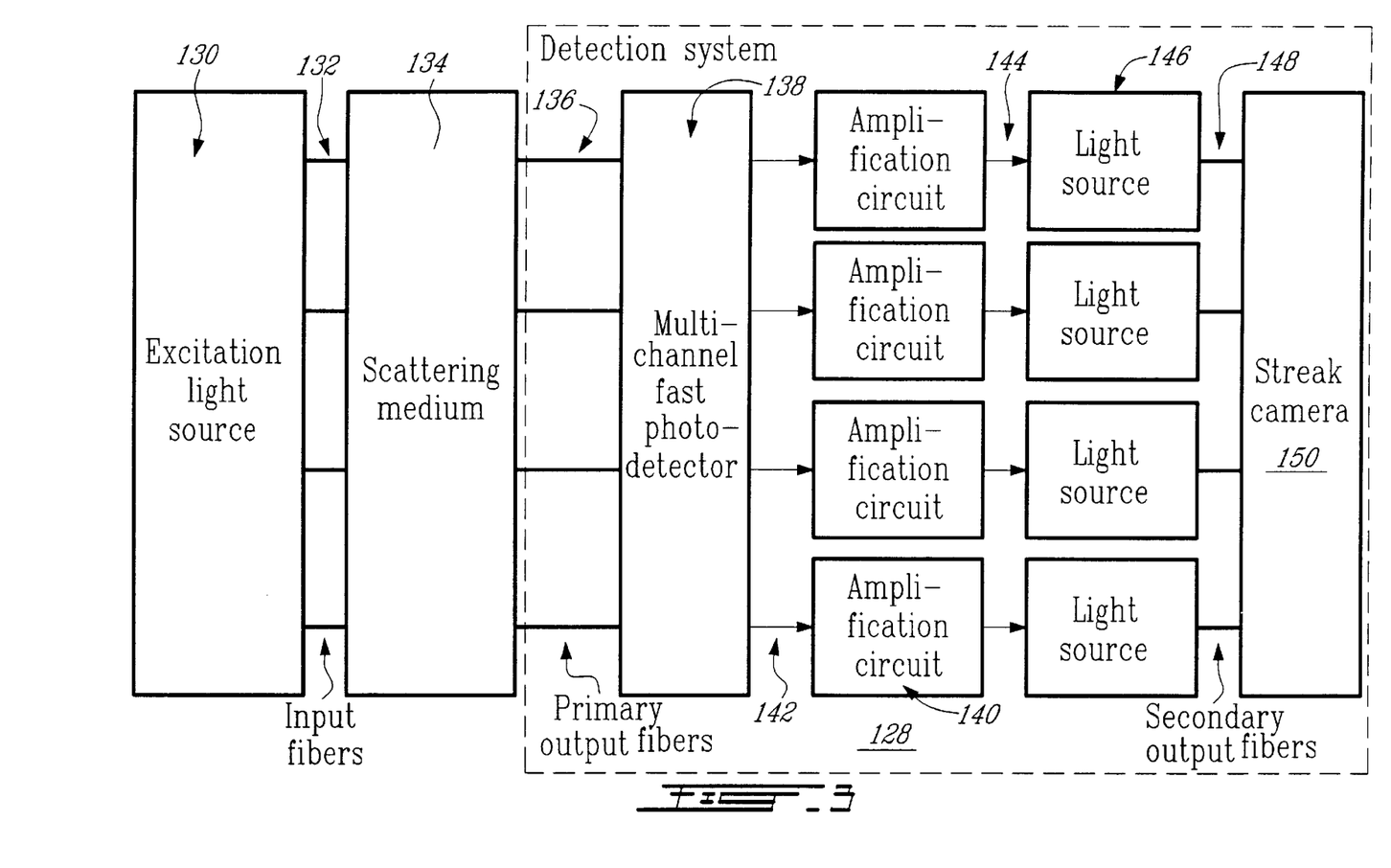
FIG. 7 is also a graph illustrating time-resolved transmittance measured through a homogeneous phantom using both the detection system of the present invention and a comparison system.

These measurements are shown in FIG. 7.

TABLE 1

Time responses of the different components of the new detection system.

| Component | Time response |
|---|---|
| Fast photo-detector (PMT R7400-02) | 0.78 ns |
| Light source (LED 1A363) | 0.5 ns |
| Amplification circuit (Pre-amplifier part) | 1.2 ns |
| Amplification circuit (LED driver part) | 1 ns |
| Overall | 1.8 ns |

As it can be soon in FIG. 7, the measurement using the new detection system is less noisy but it is also time-broadened. The time broadening can be easily explained by taking into account the time response. The measurement of the time-resolved transmittance using the comparison detection system was convoluted with a time response of 1.8 ns resulting in the dashed curve shown in FIG. 7. As can be seen, there is an excellent agreement between the time-resolved transmittance measured using the new detection system and the expected result based on a 1.8 ns time convolution. It is thus believed that using faster components, the time broadening would become negligible or acceptable, while the improvement in sensitivity would remain.

The detection system of the present invention is for time resolved trans-illumination. As indicated previously, the system comprises a fast photo detector, an amplification circuit, a light source, and a streak camera. The fast photo-detector preferably has a large detection area (>1 mm$^2$) and a fast time response (<500 ps). The amplification circuit amplifies the output signal of the fast photo-detector and generates a signal suitable for driving the light source. The light source has a fast time response (<500 ps). The streak camera allows recording the time dependence of the light emerging from the light source with a high time resolution (<500 ps).

As indicated previously, the fast photo-detector may be a fast photo multiplier tube, the light source can be a fast LED or a fast laser diode such as a VCSEL. The wavelength of the light source can be selected to correspond with the peak sensitivity of the streak camera.

In accordance with the other embodiment of the invention described herein, there is provided a multi-channel detection system. This employs a plurality of fast photo-detectors, a plurality of amplification circuits, a plurality of light sources, but a single streak camera. The plurality of fast photo-detectors can be replaced by a single multi-channel photo-detector such as a multi-anode detector.

Having now described a limited number of embodiments of the present invention, additional embodiments and modifications thereof should become apparent to those skilled in the art as defined by the appended claims.

What is claimed is:

1. A time-resolved optical imaging system for detecting light from an excitation light source through a scattering medium at a plurality of detection positions, said system comprising:
   a photo detector for receiving said light from said scattering medium and having sensitivity in a range of intensity of interest;
   an amplification circuit coupled to said photo-detector;
   an electro-optical source coupled to said amplification circuit for providing a secondary light signal; and
   a camera receiving said secondary light signal, said camera having a high temporal resolution;
   wherein said system provides said secondary light signal with an intensity suitable for good signal-to-noise quality detection by said camera for said range of intensity of interest.

2. An optical imaging system as set forth in claim 1, wherein said system is a time-resolved transillumination system, and said camera is a streak camera.

3. An optical imaging system as set forth in claim 1, wherein said photo-detector is a fast photo-detector.

4. An optical imaging system as set forth in claim 1, wherein said photo-detector comprises a photo-multiplier table.

5. An optical imaging system as set forth in claim 1, wherein said electro-optical source comprises a light emitting diode.

6. An optical imaging system as set forth in claim 1, wherein said electro-optical source comprises a laser diode.

7. An optical imaging system as set forth in claim 1, wherein the wavelength of the electro-optical source is selected to correspond with the peak sensitivity of the streak camera.

8. An optical imaging system as set forth in claim 1, including a primary output fiber for coupling from the scattering medium to the photo-detector, and a secondary output fiber for coupling from the electro-optical source to the streak camera.

9. An optical imaging system as set forth in claim 8, wherein said primary output fiber is larger in diameter than said secondary output fiber.

10. An optical imaging system as set forth in claim 9, wherein said primary output fiber collects light from the scattering medium by the use of a 3 mm-diameter fiber bundle.

11. An optical imaging system as set forth in claim 10, wherein said fiber bundle has a filling factor of about 75%.

12. An optical imaging system as set forth in claim 8, wherein the light detected at said primary output fiber is detected over a relatively large area on the order of 10 mm$^2$.

13. An optical imaging system as set forth in claim 8, wherein the secondary output fiber is small compared to the primary output fiber whereby only a small fraction of the detection area of the streak camera is used.

14. An optical imaging system as set forth in claim 1, wherein the system is a multi-channel system comprising multiple photo-detectors, multiple amplification circuits and multiple electro-optical sources.

15. An optical imaging system as set forth in claim 14, including multiple primary fibers coupling to the corresponding multiple photo-detectors, and multiple secondary fibers for coupling from the corresponding multiple electro-optical sources.

16. An optical imaging system as set forth in claim 15, wherein a single streak camera serves for all the channels.

17. An optical imaging system as set forth in claim 1, wherein said photo-detector has a large detection area greater than 1 mm$^2$.

18. An optical imaging system as set forth in claim 1, wherein said photo-detector has a fast time response less than 500 ps.

19. An optical imaging system as set forth in claim 1, wherein said electro-optical source has a fast time response less than 500 ps.

20. An optical imaging system as set forth in claim 1, where said streak camera allows recording the time dependence of the light emerging from said electro-optical source with a high time resolution less than 500 ps.

21. An optical imaging system as set forth in claim 1, wherein the system has an overall time response below 0.5 ns.

22. An optical imaging system as set forth in claim 1, wherein said system comprises:
said photo detector including multi-channel photo-detector means for receiving light from said scattering medium;
wherein said electro-optical source comprises multi-channel electro-optical converting means for converting multiple electrical signals to separate multiple secondary light signals; and
wherein said camera for receiving said multiple secondary light signals to provide an image of the scattering medium.

23. An optical imaging system as set forth in claim 22, wherein said multi-channel photo-detector means comprises-a single multi-channel photo-detector.

24. An optical imaging system as set forth in claim 23, further including a plurality of amplifier circuits interconnecting said photo-detector and said multi-channel electro-optical converting means.

25. An optical imaging system as set forth in claim 24, wherein said electro-optical converting means comprises a plurality of light emitting diodes.

26. An optical imaging system as set forth in claim 24, wherein said electro-optical converting means comprises a plurality of laser diodes.

27. An optical imaging system as set forth in claim 24, herein said photo-detector comprises a photo-multiplier tube including multiple anodes.

28. An optical imaging system as set forth in claim 24, wherein said photo-detector has a detector has a detection area greater than 1 mm$^2$.

29. An optical imaging system as set forth in claim 28, wherein said photo-detector has a response time less than 500 ps.

30. A method of detection of a transillumination image from a scattering medium, comprising the steps of:
exciting the scattering medium from an excitation light source;
photo-electrically detecting the light from the scattering medium to provide an analog electrical signal;
electro-optically converting the analog electrical signal to a secondary light signal; and
providing a camera for receiving said secondary light signal and providing an image of the scattering medium;
wherein said secondary light signal has an intensity suitable for good signal-to-noise quality detection by said camera for a range of intensity of interest of said light detected from the scattering medium.

31. A method of detection of a transillumination image from a scattering medium, as set forth in claim 30, including, between said photo-electrically detecting step and said electro-optically converting step, the step of amplifying the analog electrical signal.

32. A method of detection of a transillumination image from a scattering medium, as set forth in claim 30, wherein said detection is in a time-resolved manner.

33. A method of detection of a transillumination image from a scattering medium, as set forth in claim 30, wherein said step of photo-electrically detecting comprises collecting the emerging light from the medium over a surface area greater than 1 m$^2$.

34. A method of detection of a transillumination image from a scattering medium, as set forth in claim 30, wherein the step of photo-electrically detecting includes coupling the detected light by way of a primary optic fiber, and wherein the step of electro-optically converting includes coupling the secondary light signal by way of a secondary optic fiber.

35. A method of detection of a transillumination image from a scattering medium, as set forth in claim 34, wherein the step of photo-electrically detecting includes coupling the detected light by way of a multi-channel photo-detector with a multiple primary optic fibers coupling thereto.

36. A method of detection of a transillumination image from a scattering medium, as set forth in claim 35, wherein the step of electro-optically converting includes coupling the secondary light signal by way of a multi-channel source with multiple secondary optic fibers coupling therefrom.

37. A method of detection of a transillumination image from a scattering medium, as set forth in claim 36, wherein the step of providing a camera includes providing only a single camera accepting said multiple secondary optic fibers.

38. A method of detection of a transillumination image form a scattering medium, as set forth in claim 37, wherein the step of providing a camera includes providing a streak camera.

* * * * *